United States Patent
Bjorling et al.

(10) Patent No.: US 9,119,545 B2
(45) Date of Patent: Sep. 1, 2015

(54) ARRHYTHMIA CLASSIFICATION

(75) Inventors: Anders Bjorling, Solna (SE); Malin Hollmark, Solna (SE); Tomas Svensson, Stockholm (SE); Stefan Hjelm, Balsta (SE); Kjell Noren, Solna (SE); Karin Jarverud, Solna (SE)

(73) Assignee: St. Jude Medical, AB, Jarfalla, SW ( * ) Notice: Subject to any disclaimer, the term of this patent is extended or adjusted under 35 U.S.C. 154(b) by 1098 days.

(21) Appl. No.: 13/076,627

(22) Filed: Mar. 31, 2011

(65) Prior Publication Data
US 2011/0245701 A1 Oct. 6, 2011

Related U.S. Application Data

(60) Provisional application No. 61/348,855, filed on May 27, 2010.

(51) Int. Cl.
| | |
|---|---|
| A61B 5/04 | (2006.01) |
| A61B 5/0456 | (2006.01) |
| A61B 5/00 | (2006.01) |
| A61B 5/053 | (2006.01) |
| A61N 1/362 | (2006.01) |
| A61N 1/365 | (2006.01) |
| A61N 1/37 | (2006.01) |
| A61N 1/39 | (2006.01) |

(52) U.S. Cl.
CPC .............. *A61B 5/0456* (2013.01); *A61B 5/0031* (2013.01); *A61B 5/053* (2013.01); *A61B 5/7264* (2013.01); *A61N 1/3621* (2013.01); *A61N 1/36521* (2013.01); *A61N 1/3702* (2013.01); *A61N 1/3925* (2013.01); *A61N 1/3962* (2013.01)

(58) Field of Classification Search
USPC .................................. 607/5–7, 14, 17–18, 28
See application file for complete search history.

(56) References Cited

U.S. PATENT DOCUMENTS

| 5,117,824 A * | 6/1992 | Keimel et al. ...................... 607/4 |
| 8,321,016 B2 * | 11/2012 | Holmstrom et al. ............ 607/14 |
| 2012/0004700 A1 * | 1/2012 | Hedberg et al. ................. 607/28 |

* cited by examiner

*Primary Examiner* — Catherine Voorhees
*Assistant Examiner* — Roland Dinga

(57) ABSTRACT

An implantable medical device, is designed to collect a signal representative of the electric activity of the heart and determine a cardiogenic impedance signal for at least a portion of the heart. An R-wave detector of the IMD detects the timing of an R-wave during a cardiac cycle based on the signal representative of the electric activity. A minimum detector detects the timing of a cardiogenic impedance minimum in the cardiogenic impedance signal and within a systolic time window of the cardiac cycle. A detected arrhythmia is then classified by the IMD based on the timing of the R-wave detected by the R-wave detector and the timing of the cardiogenic impedance minimum detected by the minimum detector.

15 Claims, 5 Drawing Sheets

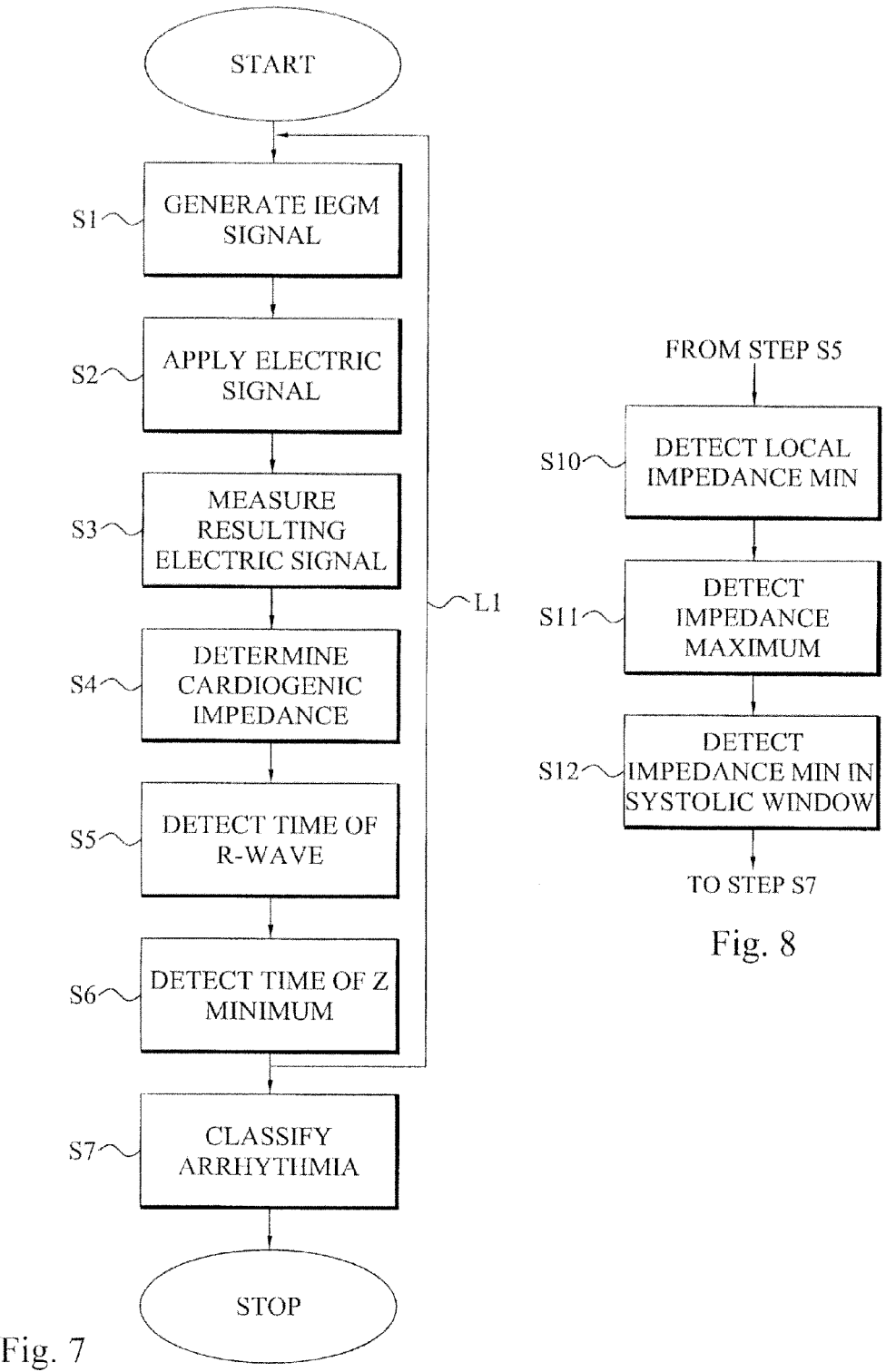

ARRHYTHMIA CLASSIFICATION

RELATED APPLICATION

The present application claims the benefit of the filing date of provisional application No. 61/348,855, filed on May 27, 2010.

BACKGROUND OF THE INVENTION

1. Field of the Invention

The present invention generally relates to arrhythmia classification, and in particular to an implantable medical device capable of detecting and classifying an arrhythmia and to an arrhythmia classification method.

2. Description of the Prior Art

Implantable medical devices (IMDs), including implantable cardioverter-defibrillators (ICDs) and pacemakers, can today be used for detecting and combating arrhythmias, such as ventricular tachyarrhythmia in IMD patients. Ventricular tachyarrhythmias, for example ventricular fibrillation or tachycardia, need to be detected as early as possible as they may otherwise lead to the death of the patient if not quickly terminated. As a consequence, once tachyarrhythmia is detected, the IMD will combat it by delivering one or more defibrillation or cardioversion shocks.

However, in several IMD and ICD patients about 5-15% of the defibrillation or cardioversion shocks are in fact unnecessary. This means that worst-case approximately one shock out of five is inappropriate for these patients. Every inappropriate shock causes decreased quality of life for patients, battery depletion of the device and potential induction of dangerous arrhythmias. Unnecessary shocks should therefore be minimized.

U.S. Pat. No. 5,311,874 discloses a method for tachycardia discrimination. In a first embodiment, a cardiac biopotential signal is recorded and processed to identify a number of feature values representing maximum and minimum values of a complex in the signal, corresponding to a complete cardiac cycle. Firstly, the complex is classified as a baseline complex or a non-baseline complex based on the cycle length of the complex. If the complex is classified as a non-baseline complex, an extensive and very complex processing of its feature values is conducted to subsequently arrive at a discrimination point in a plane defined by a similarity vector and a dissimilarity vector. Depending on where this point is in the plane, the non-baseline complex is classified as a ventricular tachycardia (VT) or non-VT complex. In a second embodiment, a corresponding complex signal processing is performed but for discriminating between hemodynamically stable and unstable ventricular tachycardias. In this case, the input signal can be a signal or condition related to the hemodynamics of the heart, such as pressure, flow or impedance.

US 2005/0154421 discloses a technique for reducing inappropriate delivery of therapy to treat ventricular tachyarrhythmias caused by supraventricular tachycardia (SVT). The document specifies that SVT can be conducted to the ventricles and lead to short ventricular cycle lengths (VCLs) that would imply ventricular tachyarrhythmia. Their technique is based on measuring multiple VCLs over a defined time period. The number of such cycles that have a length shorter than a given threshold is determined and used as a basis for detecting ventricular tachyarrhythmia. If tachyarrhythmia is detected, it is determined whether the tachyarrhythmia is due to SVT or may indeed be lethal. This determination can be based on measured VCLs and atrial cycle lengths (ACLs), measured activity level of the patient or intracardiac pressure measurements.

US 2007/0043394 discloses an IMD having circuitry for sensing cardiac signals and determining an intracardiac impedance signal. Cardiac cycles of a subject are determined based on the sensed cardiac signal and tachyarrhythmia is detected using cardiac cycle to cardiac cycle changes in a plurality of intracardiac impedance parameters obtained from the intracardiac impedance signal.

There is still a need for a technique and IMD capable of accurately classifying arrhythmias in order to select appropriate treatments or select not to apply any combating treatment to the subject.

SUMMARY OF THE INVENTION

It is an object of the invention to enable classification of arrhythmias of a patient.

It is a particular object to provide an implantable medical device capable of classifying detected arrhythmias.

These and other objectives are met by embodiments as disclosed herein.

Briefly, an embodiment relates to an implantable medical device (IMD) designed to deliver cardiac therapy to a patient's heart. The IMD has an electrode connector that is electrically connectable to multiple electrodes of which at least one is provided on a cardiac lead that can be connected to the electrode connector and the IMD. A data acquisition unit of the IMD is connected to the electrode connector and configured to capture signals representative of the electric activity of at least a portion of the heart. An R-wave detector processes this signal from the data acquisition unit for the purpose of detecting the timing of R-waves of the heart.

The IMD also has a signal generator and a signal sensing unit connected to the electrode connector. The signal generator generates an electric signal that is applicable to a portion of the heart using a connected electrode pair. The resulting electric signal is sensed by the signal sensing unit over a portion of the heart using a connected electrode pair. An impedance processor determines a cardiogenic impedance signal based on the generated and sensed electric signals.

The IMD has a minimum detector that processes the cardiogenic impedance signal for the purpose of detecting the timing of a cardiogenic impedance minimum within a systolic time window of the cardiac cycle. A detected arrhythmia is then classified based on the timing of the R-wave detected by the R-wave detector and the timing of the cardiogenic impedance minimum detected by the minimum detector.

Another embodiment relates to a method of classifying an arrhythmia of a patient's heart. The method involves generating a signal representative of the electric activity of at least a portion of the heart and detecting the timing of an R-wave of a cardiac cycle in this signal. An electric signal is applied to the heart and the resulting electric signal is sensed for the purpose of determining a cardiogenic impedance signal. The impedance signal is processed in order to identify the timing of a cardiogenic impedance minimum within a systolic time window of the cardiac cycle. The timings of the R-wave and the cardiogenic impedance minimum are employed in order to classify a detected arrhythmia.

BRIEF DESCRIPTION OF THE DRAWINGS

FIG. 7 is a flow diagram illustrating a method of classifying arrhythmia according to an embodiment.

FIG. 8 is a flow diagram illustrating an embodiment of the step of detecting timing of cardiogenic impedance minimum in FIG. 7.

DESCRIPTION OF THE PREFERRED EMBODIMENTS

Figures 1, 3:
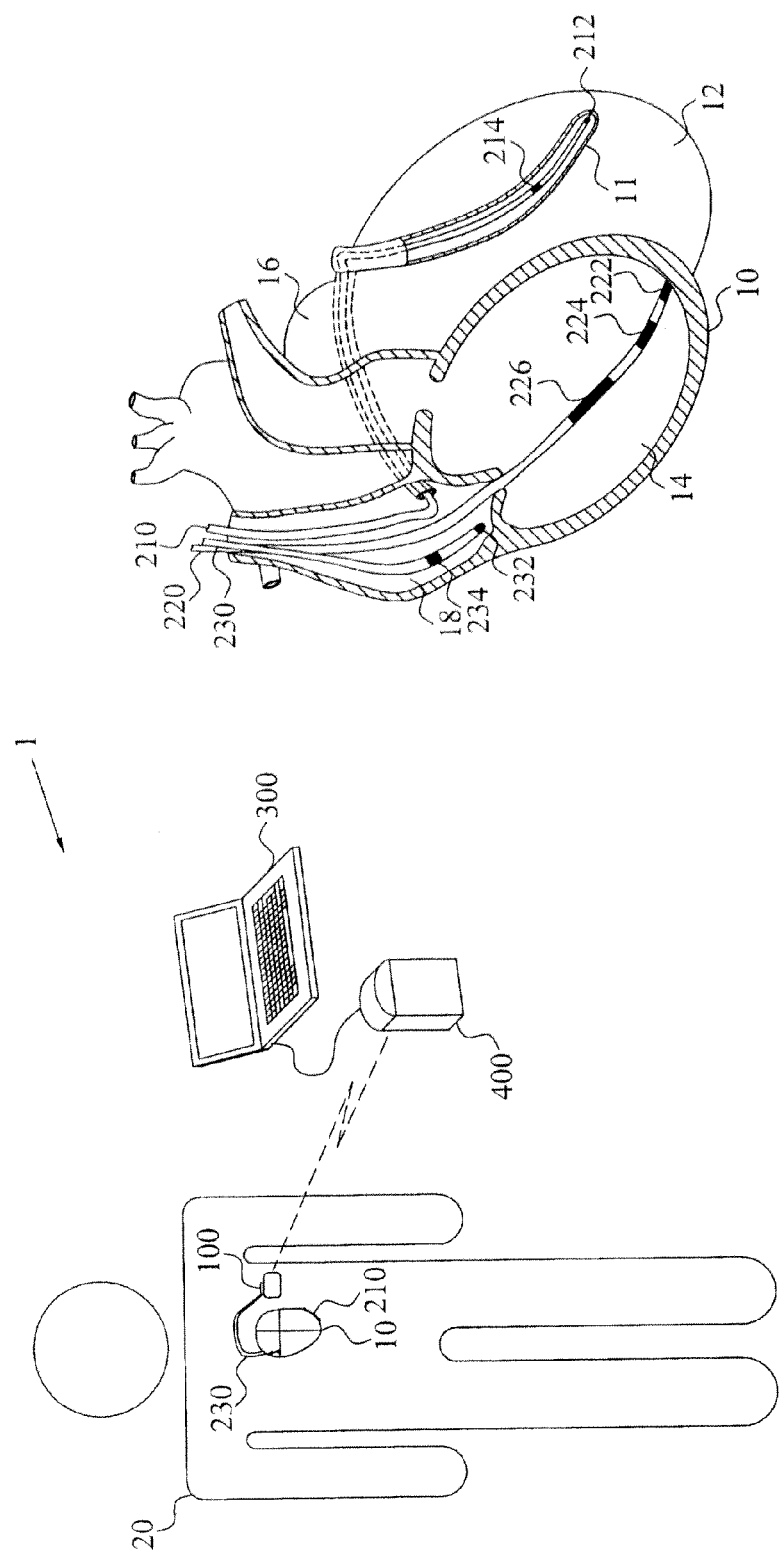
FIG. 1 is a schematic overview of an implantable medical device in a human subject and a non-implantable data processing unit capable of conducting wireless communication with the implantable medical device.
FIG. 3 is an illustration of a lead configuration applicable according to an embodiment.

Throughout the drawings, the same reference numbers are used for similar or corresponding elements.

The present invention generally relates to arrhythmia classification and in particular to implantable medical devices and methods capable of classifying an arrhythmia of a patient's heart and thereby provide relevant diagnostic information that can be useful in selecting an appropriate treatment scheme to combat the arrhythmia, Arrhythmia or cardiac dysrhythmia is a large and heterogenous group of conditions in which there is abnormal electrical activity in the heart. For instance, the heart may beat too fast or too slow, and may be regular or irregular. There is therefore a need for a technique that allows discrimination and classification between different forms of arrhythmia to thereby select the most appropriate treatment scheme to combat a detected and classified arrhythmia.

For instance, ventricular tachyarrhythmia relates to medical conditions in which the electrical activity of the heart is irregular and/or faster than normal and where the abnormal activity originates from or is caused by the left and/or right ventricle. Ventricular tachyarrhythmias are traditionally defined as ventricular tachycardia, ventricular flutter and ventricular fibrillation.

Ventricular tachycardia is a potentially life threatening cardiac tachyarrhythmia originating in the ventricles. The tachycardia is characterized by increased heart rate, often in the interval of 120 to 250 beats per minutes. It may degrade into the more serious ventricular fibrillation.

Ventricular flutter is a ventricular tachyarrhythmia characterized electrocardiographically by smooth undulating waves with QRS complexes merged with T waves, and a rate of approximately 250 beats per minute. If untreated it usually progresses to ventricular fibrillation.

Ventricular fibrillation is a condition with uncoordinated contraction of the cardiac muscle of the ventricles in the heart. As a result, the heart fails to adequately pump the blood and hypoxia may occur. If continuing for more than a few seconds, blood circulation and blood pressure will drop significantly.

Ventricular flutter and fibrillation should, typically, be treated immediately with a defibrillation shock. However, for other types of ventricular tachyarrhythmias it might be sufficient to use an anti-tachycardia pacing (ATP) scheme in order to combat the ventricular tachyarrhythmia and no shock is needed. An ATP-based treatment scheme is generally preferred from the patient point of view as shocks are unpleasant to the patient and further drains power from the battery of the ICD.

In an embodiment, an arrhythmia classification differentiates between so called hemodynamically stable arrhythmias, such as stable ventricular tachyarrhythmias, and hemodynamically unstable arrhythmias, such as unstable ventricular tachyarrhythmias. Stable and unstable arrhythmias are also denoted non-hemodynamically and hemodynamically compromising arrhythmias in the art, respectively.

For instance, a hemodynamically stable form of ventricular tachyarrhythmias is typically characterized by stable blood pressure or only temporarily and slightly decreasing (typically less than 20%, preferably less than 10%, such as less than 5% or less than 1%) blood pressure. However, lethal and unstable forms of ventricular tachyarrhythmias, in clear contrast, lead to large drops in blood pressure, typically with about or even more than 50%. In severe conditions, the blood pressure could even fall as low as 50 mmHg for the systolic pressure.

In another embodiment, the arrhythmia classification can be performed in order to discriminate between supraventricular tachyarrhythmias (SVTs) and ventricular tachyarrhtyhmias (VTs). A SVT is a tachycardiac rhythm originating above the ventricular tissue. The SVT can be from a sinoatrial source, an atrial source or an atrioventricular source. In contrast to VTs, SVTs can often be left without any shocking and self-terminates. Thus, the treatment scheme for a classified SVT most often differ from the treatment scheme that is most appropriate for a classified VT. Shock therapy for SVT is generally considered as inappropriate.

The above listed embodiments of arrhythmia classification, i.e. based on a hemodynamic assessment or based on the origin of the arrhythmia, should be seen as preferred but non-limiting examples of different arrhythmia types or classes that can be identified by the embodiments. In the following these examples will be employed to illustrate different embodiments of the invention.

FIG. 1 is a schematic overview of a system 1 that includes an implantable medical device (IMD) 100 according to the embodiments and a non-implantable data processing device 300. In the figure, the IMD 100 is illustrated implanted in a human patient 20 and as a device that monitors and/or provides therapy to the heart 10 of the patient 20. The patient 20 must not necessarily be a human patient but can instead be an animal patient, in particular a mammalian patient, in which an IMD 100 can be implanted. The IMD 100 can be in the form of a pacemaker, cardiac defibrillator or cardioverter, such as implantable cardioverter-defibrillator (ICD). The IMD 100 is, in operation, connected to one or more, two in the figure, intracardiac leads 210, 230 inserted into different heart chambers, the right atrium and left ventricle in the figure.

FIG. 1 also illustrates an external data processing device 300, such as programmer or clinician's workstation, that can communicate with the IMD 100, optionally through a communication device 400 that operates similar to a base station on behalf of the data processing device 300. As is well known in the art, such a data processing device 300 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the data processing device 300 before display to a clinician. In the light of the present invention, such diagnostic data can include cardiogenic impedance data generated by the IMD 100, arrhythmia classification data and/or other diagnostic data relating to arrhythmia detection and classification.

Figure 2:
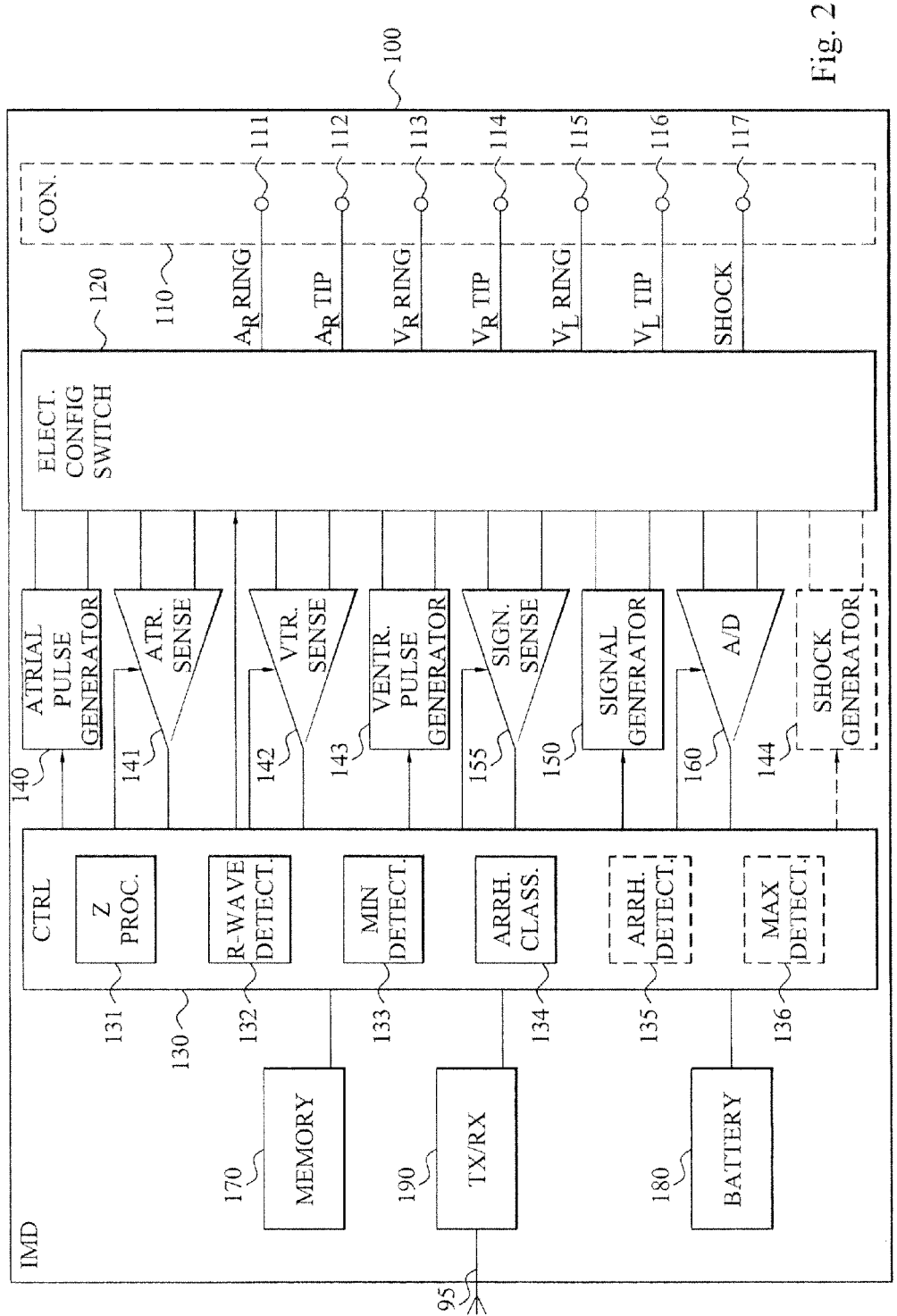
FIG. 2 is a block diagram of an embodiment of an implantable medical device.

FIG. 2 illustrates an embodiment of an IMD 100 suitable for delivering cardiac therapy to a heart of a subject. FIG. 2 is a simplified block diagram depicting various components of the IMD 100. While a particular multi-chamber device is shown in the figure, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination to provide an IMD capable of treating the appropriate heart chamber(s) with pacing stimulation and also cardioversion and/or defibrillation.

The IMD 100 has a housing, often denoted as can or case in the art. The housing can act as return electrode for unipolar leads, which is well known in the art. The IMD 100 also comprises an electrode connector or input/output (I/O) 110 having, in this embodiment, a plurality of terminals 111-117. With reference to FIGS. 2 and 3, the lead connector 110 is configured to be, during operation in the subject body, electrically connectable to, in this particular example, a right atrial lead 230, a left ventricular lead 210 and a right ventricular lead 220. The electrode connector 110 consequently comprises terminals 111, 112 that are electrically connected to matching electrode terminals of the atrial lead 230 when the atrial lead 230 is introduced in the lead connector 110. For instance, one of these terminals 112 can be designed to be connected to a right atrial tip terminal of the atrial lead 230, which in turn is electrically connected through a conductor running along the lead body to a tip electrode 232 present at the distal end of the atrial lead 230 in the right atrium 18 of the heart 10. A corresponding terminal 111 is then connected to a right atrial ring terminal of the atrial lead 230 that is electrically connected by another conductor in the lead body to a ring electrode 234 present in connection with the distal part of the atrial lead 230, though generally distanced somewhat towards the proximal lead end as compared to the tip electrode 232.

In an alternative implementation, the IMD 100 is not connectable to a right atrial lead 230 but instead to a left atrial lead configured for implantation in the left atrium 16. A further possibility is to have an IMD 100 with an electrode connector 110 having sufficient terminals to allow the IMD 100 to be electrically connectable to both a right atrial lead 230 and a left atrial lead. Though, it is generally preferred to have at least one electrically connectable atrial lead in order to enable atrial sensing and pacing, the IMD 100 does not necessarily have to be connectable to any atrial leads. In such a case, the terminals 111, 112 of the electrode connector 110 can be omitted.

In order to support right chamber sensing and pacing, the lead connector 110 further comprises a right ventricular tip terminal 114 and a right ventricular ring terminal 113, which are adapted for connection to a right ventricular tip electrode 222 and a right ventricular ring electrode 224 of the right ventricular lead 220 implantable in the right ventricle 14, see FIG. 3.

In an alternative embodiment, the lead connector 110 is instead or also connectable to a left ventricular lead 210. A left ventricular lead 210 is typically implanted in the coronary venous system 11 for safety reasons although implantation inside the left ventricle 12 has been proposed in the art. In the following, "left ventricular lead" 210 is used to describe a cardiac lead designed to provide sensing and pacing functions to the left ventricle 12 regardless of its particular implantation site, i.e. inside the left ventricle 12 or in the coronary venous system 11. The left ventricular lead 210 preferably also comprises a tip electrode 212 and a ring electrode 214 electrically connectable to corresponding terminals 115, 116 of the electrode connector 110.

The electrode connector 110 preferably also has a terminal 117 configured to be electrically connectable to a shock electrode 226 preferably provided on the right atrial lead 220, the left ventricular lead 210 or the right atrial lead 230. The electrode connector 110 can alternatively have multiple terminals 117 configured to be electrically connectable to multiple shock electrodes, if more than one of the connectable leads 210, 220, 230 is equipped with such a shock electrode 226 configured to deliver a defibrillation/cardioversion shock.

Any of the right ventricular lead 220 and the left ventricular lead 210 can be a so-called multi-electrode ventricular lead. In such a case, the lead generally has multiple ring electrodes provided at different positions along the lead. The electrode connector 110 then has to have appropriate number of terminals for electrical connection to these multiple electrodes.

The housing can act as return electrode as mentioned above. In such a case, the electrode connector 110 can have a dedicated terminal (not illustrated) connected to the housing.

The IMD 100 as illustrated in FIG. 2 comprises an optional atrial pulse generator 140 and an optional ventricular pulse generator 143 that generate pacing pulses for delivery by the atrial lead(s) and the ventricular lead(s) preferably through an electrode configuration switch 120, It is understood that in order to provide stimulation therapy in different heart chambers, the atrial and ventricular pulse generators 140, 143 may include dedicated, independent pulse generators, multiplexed pulse generators, or shared pulse generators. The pulse generators 140, 143 are controlled by a controller 130 via appropriate control signals, respectively, to trigger or inhibit the stimulating pulses.

The IMD 100 also comprises the controller 130, preferably in the form of a programmable microcontroller 130 that controls the operation of the IMD 100. The controller 130 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 130 is configured to process or monitor input signal as controlled by a program code stored in a designated memory block. The type of controller 130 is not critical to the described implementations. In clear contrast, any suitable controller may be used that carries out the functions described herein. The use of microprocessor-based control circuits for performing timing and data analysis functions are well known in the art.

The controller 130 further controls the timing of the stimulating pulses, such as pacing rate, atrioventricular interval (AVI), atrial escape interval (AEI) etc. as well as to keep track of the timing of refractory periods, blanking periods, noise detection windows, evoked response windows, alert intervals, marker channel timing, etc.

A preferred electronic configuration switch 120 includes a plurality of switches for connecting the desired terminals 111-117 to the appropriate I/O circuits, thereby providing complete electrode programmability. Accordingly, the electronic configuration switch 120, in response to a control signal from the controller 130, determines the polarity of the stimulating pulses (e.g., unipolar, bipolar, combipolar, etc.) by selectively closing the appropriate combination of switches (not shown) as is known in the art.

An optional atrial sensing circuit or detector 141 and an optional ventricular sensing circuit or detector 142 are also selectively coupled to the atrial lead(s) and the ventricular lead(s) through the switch 120 for detecting the presence of cardiac activity in the heart chambers. Accordingly, the atrial and ventricular sensing circuits 141, 142 may include dedicated sense amplifiers, multiplexed amplifiers, or shared amplifiers. The switch 120 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 141, 142 preferably employs one or more low power, precision amplifiers with programmable gain and/or automatic gain control, band-pass filtering, and a threshold detection circuit, as known in the art, to selectively sense the cardiac signal of interest.

The outputs of the atrial and ventricular sensing circuits 141, 142 are connected to the controller 130, which, in turn, is able to trigger or inhibit the atrial and ventricular pulse generators 140, 143, respectively, in a demand fashion in response to the absence or presence of cardiac activity in the appropriate chambers of the heart.

Furthermore, the controller 130 is also capable of analyzing information output from the sensing circuits 141, 142 and/or a data acquisition unit 160 to determine or detect whether and to what degree tissue capture has occurred and to program a pulse, or pulse sequence, in response to such determinations. The sensing circuits 141, 142, in turn, receive control signals over signal lines from the controller 130 for purposes of controlling the gain, threshold, polarization charge removal circuitry, and the timing of any blocking circuitry coupled to the inputs of the sensing circuits 141, 142 as is known in the art.

According to the embodiments cardiac signals are applied to inputs of a data acquisition unit 160 connected to the electrode connector 110. The data acquisition unit 160 is preferably in the form of an analog-to-digital (A/D) data acquisition unit 160 configured to acquire intracardiac electrogram (IEGM) signals, convert the raw analog data into a digital signal, and store the digital signals for later processing and/or transmission to the programmer by a transceiver 190. The data acquisition unit 160 is coupled to the atrial lead and/or the ventricular lead through the switch 120 to sample cardiac signals across any pair of desired electrodes.

The IMD 100 also has a signal generator 150 connectable to two of the terminals 111-117 preferably through the switch 120. The signal generator 150 is configured to generate an electric signal that is applicable over two electrodes arranged in connection with the patient's heart. Thus, the generated electric signal is forwarded by the switch 120 to two of the terminals 111-117 and further to the corresponding electrodes connectable to the selected terminals.

The electric signal is preferably an AC signal having a defined time-dependent voltage/current profile. The electric signal is preferably a sub-threshold electric signal implying that it is not intended to trigger capture by the myocardium when applied to the heart. This is in clear contrast to the pacing pulses generated by the atrial 140 and ventricular 143 pulse generator.

In the figure the signal generator 150 has been illustrated as a stand-alone signal generator 150 controlled by the controller 130. In an alternative approach, the relevant sub-threshold AC signal could instead be generated by the atrial 140 or ventricular 143 pulse generator, thereby relaxing the need for a further generator 150 of the IMD 100. In such a case, the controller 130 controls the atrial 140 or ventricular 143 pulse generator to generate the electric signal having characteristics, i.e. duration and amplitude, which generally differ from the pacing pulses otherwise generated by the pulse generator 140, 143.

A signal sensing unit 155 is implemented preferably connected to the switch 120 and thereby to two electrode terminals connected to two electrodes. The sensing unit 155 is configured to sense a resulting electric signal captured over the two electrodes. The resulting electric signal is preferably a resulting AC signals originating from at least a portion of the heart. This sensed AC signals is further generated due to the applied AC signal generated by the signal generator 150.

An impedance processor 131 is implemented in the IMD 100 and configured to determine a cardiogenic impedance signal of the heart based on the electric signal generated by the signal generator 150 and the resulting electric signal sensed by the signal sensing unit 155. In a particular embodiment, the impedance processor 131 generates the cardiogenic impedance signal based on the current of the electric signal and the measured or sensed voltage of the resulting electric signals according to techniques well known in the art. The cardiogenic impedance signal is representative of the impedance as measured over a portion of the heart.

The cardiogenic impedance signal is preferably a band-passed version of the calculated impedance signal in order to remove or at least suppress the respiratory contribution to the impedance signal. The cardiogenic impedance signal is further preferably characterized by not having any DC component, i.e. its average value is zero.

As known in the art, bipolar, tripolar or quadropolar impedance signals can be determined. In a bipolar setting the same pair of electrodes is used by both the signal generator 150 for signal application as for the signal sensing unit 155 for sensing the resulting electric signals. Bipolar impedance signals are in particular reflective of the local environment around the electrodes. Tripolar settings have a common electrode between signal application and signal sensing, whereas quadropolar settings use two electrodes for signal application and two other electrodes for signal sensing. Tripolar and quadropolar impedance signals are more reflective of global properties affecting the impedance as compared to the bipolar impedance signals.

Animal experiments have been conducted with various impedance vectors and settings. The impedance vectors that were determined to be best suited to differentiate the various arrhythmias can be selected among right ventricular (RV) tip-RV coil bipolar, right atrial (RA) tip-RA ring bipolar, RV tip-RV ring bipolar and RA (ring or tip)-left ventricular (LV) (ring or tip) bipolar. These bipolar settings work well. The embodiments are though not limited to these particular impedance configurations but can be applied to other bipolar settings and also tripolar and quadropolar configurations.

The IMD 100 further comprises an R-wave detector 132 that is configured to process the signal representative of the electric activity of the heart and collected by the data acquisition unit 160. The R-wave detector 132 is in particular configured to detect the presence of an R-wave of a QRS complex during a cardiac cycle using the signal representative of the electric activity. The timing or time point of this R-wave is further determined by the R-wave detector 132 preferably based on information of the sample number of the sample coinciding with the R-wave and collected by the data acquisition unit 160. The sample number can be used directly as timing parameter or can be converted into value expressed in seconds or some other time unit based on information of the sampling frequency of the data acquisition unit 160.

The R-wave is easily identified in the signal recorded by the data acquisition unit 160 as a sudden and significant change in the signal corresponding to the ventricular depolarization.

A minimum detector 133 is implemented in the IMD 100 and configured to detect a cardiogenic impedance minimum based on the cardiogenic impedance signal from the impedance processor 131. In more detail, the minimum detector 133 is configured to detect the minimum in the cardiogenic impedance within a systolic time window of a cardiac cycle.

This processing of the cardiogenic impedance signal by the minimum detector 133 can, in an embodiment, be implemented according to the following scheme. The minimum detector 133 first identifies the impedance signal sample that coincides with the start of the systolic time window. Once the impedance sample that corresponds to the start of the systolic time window has been identified, the minimum detector 133 identifies those impedance signal samples that fall within the systolic time window. The minimum detector 133 can then simply go through these identified samples in order to identify the one that has the smallest impedance value. The sample number of this sample with the smallest impedance value can then be used directly as timing or time parameter of the cardiogenic impedance minimum. Alternatively, the sample number is converted into a time parameter in seconds or some other time unit by means of the impedance sampling frequency.

An arrhythmia classifier 134 is configured to use the timing of the R-wave as detected by the R-wave detector 132 and the timing of the cardiogenic impedance minimum as detected by the minimum detector 133 in order to classify an arrhythmia of the heart. Thus, the arrhythmia classification of the embodiments uses two timings or time parameters, one corresponding to the R-wave of a cardiac cycle and the other corresponding to a minimum in the cardiogenic impedance signal within the cardiac cycle and within the systolic time window.

In a particular embodiment the arrhythmia classifier 134 is configured to classify an arrhythmia based on a time interval defined from the timing of the R-wave to the timing of the cardiogenic impedance minimum.

In a preferred embodiment, the systolic time window is defined using extreme values in the cardiogenic impedance signal. In such a case, the minimum detector 133 is first configured to detect a local cardiogenic impedance minimum within a defined time window centered at the timing of the R-wave detected by the R-wave detector 132.

This processing of the cardiogenic impedance signal by the minimum detector 133 can, in an embodiment, be implemented according to the following scheme. The minimum detector 133 first identifies the impedance signal sample that coincides with the timing of the R-wave as determined by the R-wave detector 132. This can easily be performed if the minimum detector 133 has access to the respective sampling frequencies employed by the data acquisition unit 160 and the impedance processor 131. Once the impedance sample that corresponds to the timing of the R-wave has been identified, the minimum detector 133 identifies those impedance signal samples that fall within the time window centered at the timing of the R-wave. The minimum detector 133 can then simply go through these identified samples in order to identify the one that has the smallest impedance value in order to detect the local cardiogenic impedance minimum within the defined time window.

Animal experiments confirm that a defined time window centered around the timing of the R-wave of preferably 100 ms works well. It means that the relevant time window in which the local cardiogenic impedance minimum is searched is preferably ±50 ms relative the timing of the R-wave. This close to the R-wave the blood flow is under normal conditions low (isovolumetric contraction). The cardiogenic impedance is, among others, affected by the blood flow. As a consequence, characteristic changes in the derived impedance parameter are therefore easier to detect within this time window.

Although the above presented size of the time window is a preferred implementation parameter, the embodiments are not limited thereto. In clear contrast, experimental data can be utilized in order to derive a suitable time window size, including patient-specific window size, that, though, should be larger than zero by shorter than the time length of a cardiac cycle.

The local cardiogenic impedance minimum marks the start of the systolic time window. In an alternative approach, the start of the systolic time window is at a fixed time interval following the local cardiogenic impedance minimum. For instance, the start of the systolic time window can be 10 ms after the timing of the local cardiogenic impedance minimum. In such a case, the cardiogenic impedance minimum within the systolic time window can never be equal to the local cardiogenic impedance minimum within the detection window.

The end of the systolic time window is then searched within a virtual cardiac cycle. This virtual cardiac cycle starts with the start of the systolic time window, i.e. the local cardiogenic impedance minimum or optionally a fixed time interval past the timing of the local cardiogenic impedance minimum, and ends with the timing of the R-wave of the next, following cardiac cycle. In an alternative embodiment the virtual cardiac cycle does not necessarily end with the timing of the next R-wave but rather at the timing of the next R-wave plus a delta. This delta is preferably equal to the timing of the current R-wave subtracted by the timing of the local cardiogenic impedance minimum within the defined detection window. With a detection window of 100 ms this implies that the end of the virtual cardiac cycle will be at most 50 ms before or after the timing of the next R-wave.

The virtual cardiac cycle therefore does not extend from R-wave to R-wave as the true cardiac cycle.

An optional but preferred maximum detector 136 is configured to detect a cardiogenic impedance maximum within the search window corresponding to the virtual cardiac cycle. Thus, the maximum detector 136 searches for the cardiogenic impedance maximum among the impedance samples from the local cardiogenic impedance minimum or optionally at a fixed time interval past the local cardiogenic impedance minimum and the impedance sample coinciding with the timing of the R-wave of the next true cardiac cycle or optionally at the timing of the next R-wave plus the previously mentioned delta. The search for the cardiogenic impedance maximum can simply be implemented by going through all the impedance samples within the search window and then identify the impedance sample corresponding to the largest impedance value.

The start and end of the systolic time window are now found, i.e. the local cardiogenic impedance minimum within the predefined time window centered at the timing of the R-wave or optionally at the timing of the local cardiogenic impedance minimum plus a fixed time interval and the global cardiogenic impedance maximum within the search window. The minimum detector 133 can now identify the cardiogenic impedance minimum within this systolic time window. The minimum detector 133 can simply go through the impedance samples within the systolic time window in order to identify the one that corresponds to the lowest impedance value. The sample number of this sample with the smallest impedance value can then be used directly as timing or time parameter of the cardiogenic impedance minimum. Alternatively, the sample number is converted into a time parameter in seconds or some other time unit by means of the impedance sampling frequency.

Figure 4:
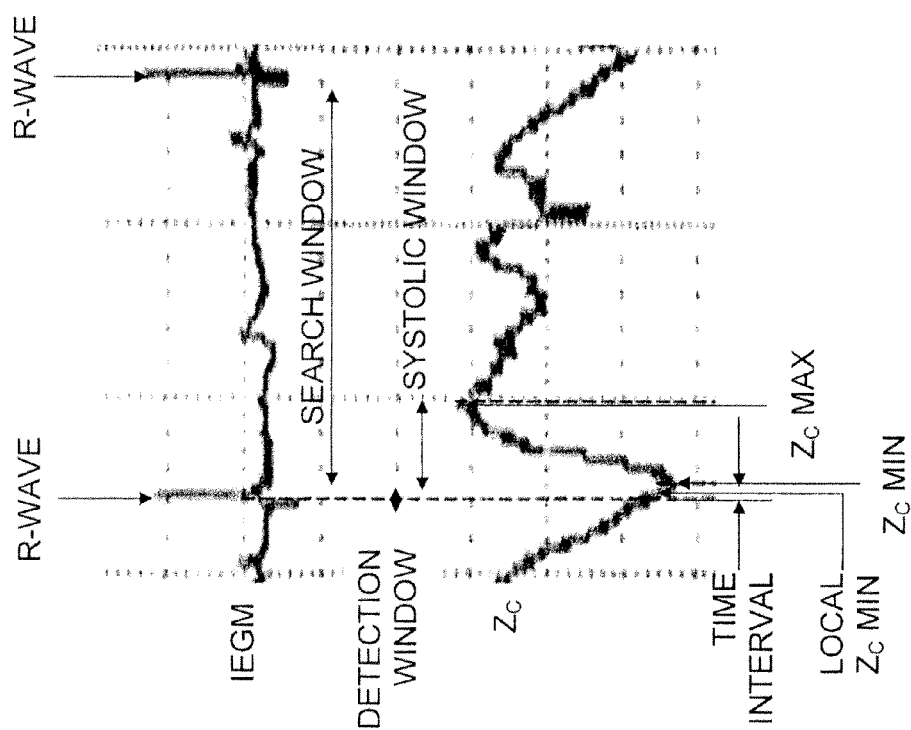
FIG. 4 schematically illustrates an IEGM signal and a synchronized cardiogenic impedance signal.

This concept is schematically illustrated in FIG. 4. The figure illustrates an IEGM signal recorded by the data acquisition unit 160. The occurrence of R-waves within two consecutive cardiac cycles is indicated in the IEGM signal. A time window or detection window is centered at the time of the R-wave and is indicated in the figure. The lower part of FIG. 4 illustrates the cardiogenic impedance signal determined by the impedance processor 131. The local minimum in the cardiogenic impedance signal within the detection window and the maximum in the cardiogenic impedance signal within the search window are marked in the window as local $Z_C$ min and $Z_C$ max, respectively. The cardiogenic impedance minimum in the systolic time window is marked as $Z_C$ min in the figure. The preferred arrhythmia classification parameter in the form of the time interval between the timing of the R-wave and the timing of the cardiogenic impedance minimum is also indicated in FIG. 4.

In a simpler implementation algorithm, the systolic window and the search window are not started at the timing of the local cardiogenic impedance minimum within the detection window or at the fixed time interval past the timing of the local cardiogenic impedance minimum. In clear contrast, the start of these two time windows is instead the start of the detection window, e.g. preferably the timing of the R-wave—50 ms. This leads to a simpler algorithm since no local cardiogenic impedance minimum must then be determined. The search window will then extend from the start of the detection window (R-wave—50 ms) and up to the next R-wave or the timing of the next R-wave plus delta. Correspondingly, the systolic window will then extend from the start of the detection window and up to the maximum in the cardiogenic impedance signal within the search window.

The classification parameter of the embodiments is related to an intrinsic electro-mechanical delay of the heart. The cardiogenic impedance signal, although generally hard to interpret, contains mechanical information. The mechanical information can, for instance, be local wall movement in the case of a bipolar impedance signal, more global volume or wall movement information in case of a quadropolar impedance signal. Properties of surrounding tissue, the amount of surrounding blood and electrode movements also affect the cardiogenic impedance signal.

The cardiogenic impedance signal represents mechanical information of the heart, whereas the IEGM signal, on the other hand, is simply electrical in nature. Thus, by using the R-wave information from the IEGM signal and the cardiogenic impedance signal, the time parameter as determined by the arrhythmia classifier 134 relates to an electromechanical coupling for the heart.

Animal experiments have been performed and confirm that this particular time parameter is a highly effective classification parameter in order to discriminate between different types of arrhythmias, such as discriminate between hemodynamically stable and unstable arrhythmia and discriminate between arrhythmia origins, such as SVTs versus VTs.

The IMD 100 preferably comprises a shock generator 144 that is configured to generate a defibrillation/cardioversion shock that is to be applied to the heart using a shock electrode electrically connectable to the terminal 117 of the electrode connector 110. The operation of the shock generator 144 is controlled by the controller 130. The controller 130 then performs this control dependent on the arrhythmia classification of the arrhythmia classifier 134. As a consequence, a class specific arrhythmia treatment is thereby achieved. For instance, an arrhythmia can be classified by the arrhythmia classifier 134 as being hemodynamically stable or unstable. In such a case, the controller 130 preferably activates the shock generator 144 to trigger generation and application of a shock if the arrhythmia classifier classifies an arrhythmia as a hemodynamcially unstable arrhythmia. Correspondingly, if the arrhythmia classifier 134 instead classifies an arrhythmia as being hemodynamically stable, the controller 130 preferably prevents the shock generator 144 from generating and applying a shock. In this latter case no anti-arrhythmia treatment is applied to the heart. Alternatively, non-shock arrhythmia treatment, such as ATP, could instead by selected to be appropriate for the hemodynamically stable arrhythmia. The controller 130 then activates the ventricular pulse generator 143 and/or the atrial pulse generator 140 to generate and apply the ATP to the heart using electrodes selected by the controller 130 through control of the switch 120.

Correspondingly, if the arrhythmia classifier 134 is capable of classifying an arrhythmia as being a SVT or a VT, the operation of the shock generator 144 can be controlled by the controller 130 based on the classification result from the arrhythmia classifier 134. In a preferred implementation, the controller activates the shock generator 144 to generate and apply a shock if the arrhythmia classifier 134 classifies the arrhythmia as a VT. If the arrhythmia classifier 134 instead classifies the arrhythmia as a SVT or a mild VT at low cardiac rate, the controller 130 preferably prevents the shock generator 144 from generating and applying a shock to combat the arrhythmia. In comparison to above, no anti-arrhythmia is applied at all to combat the SVT or a non-shock anti-arrhythmia treatment scheme, such as ATP, is instead selected by the controller 130.

Classification of an arrhythmia as hemodynamically stable versus unstable and SVT versus VT can of course be combined. Thus, a SVT or VT can be classified as a hemodynamically stable or unstable SVT or VT.

The signal generator 150 and the signal sensing unit 155 can be configured to operate continuously or periodically in order to enable a continuous or periodic acquisition of the cardiogenic impedance signal. However, such a procedure generally drains quite a lot of power from the battery 180 of the IMD 100. Therefore, a preferred implementation embodiment in particular collects the cardiogenic impedance signal when there is a need thereof, i.e. in connection with an arrhythmia event.

The IMD 100 therefore preferably has an arrhythmia detector 135 configured to detect an arrhythmia of the heart. The arrhythmia detector 135 preferably performs this arrhythmia detection based on a heart rate of the heart as obtained from the IEGM signal from the data acquisition unit 160. Thus, by continuously, periodically or intermittently monitoring the current heart rate of the patient using the IEGM signal, the arrhythmia detector 135 can detect whether an arrhythmia event is present or not. The arrhythmia detector 135 may also base the arrhythmia detection on further input information, such as data from an activity sensor (not illustrated) provided inside or connected to the IMD 100.

In such a case, the R-wave detector 132 is preferably responsive to the arrhythmia detector 135 and is configured to detect the R-wave of a cardiac cycle and determine its timing in response to the arrhythmia detector 135 detecting an arrhythmia event. Also the minimum detector 133 is preferably responsive to the arrhythmia detector 135 and configured to detect the cardiogenic impedance minimum and determine its timing in response to the arrhythmia detector 135 detecting the arrhythmia event. Also the operation of the signal generator 150, the signal sensing unit 155, the impedance processor 131 and the maximum detector 136 can be made responsive to the arrhythmia detector 135 detecting an arrhythmia event similar to the operation of the R-wave detector 132 and the minimum detector 133.

The arrhythmia classification based on the time interval parameter by the arrhythmia classifier 134 is preferably conducted based on a comparison of the time interval with a time threshold. Thus, the arrhythmia is classified as a type 1 arrhythmia or a type 2 arrhythmia based on whether the time interval exceeds or is smaller than the time threshold.

The particular time parameter employed in the preferred comparison by the arrhythmia classifier can be generic or specific. In the former case, the time interval parameter is determined for different arrhythmia events in a patient population. Information from the patients and/or diagnostic data collected in connection with the arrhythmia events is then utilized by a physician in order to try to classify the arrhythmia as correctly as possible. In such a case, data from this whole patient population can be utilized in order to derive a generic time threshold that can be programmed into the IMD, such as transmitted to the transceiver 190 and stored in a memory 170 accessible to the arrhythmia classifier 134. In an alternative approach, the time threshold is a patient specific threshold, In such a case, information from the patient and/or diagnostic data collected in connection with the arrhythmia events is utilized by a physician in order to classify the arrhythmia events as in above, The difference now is that the data originates from a single patient. Valuable data that can be used for determining patient specific time thresholds can be collected at the time of implantation of the IMD 100. Today it is practice to trigger arrthythmias when implanting the IMD 100 in order to verify that the IMD 100 correctly detects the arrhythmia and initiates a pre-programmed anti-arrhythmia treatment. The time parameter can then be determined during these triggered arrhythmia events in order to define a suitable value for the time threshold.

The time threshold does not necessarily have to be a static value but can instead be dynamically adjusted and tuned in order to derive as a correct threshold value as possible. The IMD 100 can, for instance, be programmed to derive the time interval parameter for the first X detected arrhythmia events. The time interval parameters for these first X arrhythmias are then not employed in order to select appropriate anti-arrhythmia treatment but are instead utilized in order to calculate a suitable time threshold. The time intervals determined by the arrhythmia classifier for these X arrhythmias are preferably uploaded by the transceiver 190 to the data processing unit of the physician. The physician uses the received data together with other patient data from the IMD 100 and/or from the patient himself/herself in order to try to classify the arrhythmias and find an appropriate time threshold. The determined time threshold is then downloaded to the IMD 100 and can be utilized in arrhythmia classification by the arrhythmia classifier 134 for any following arrhythmias in the patient. The parameter X can be pre-programmed in the IMD or determined by the physician. Generally, a value of 5-10 should be sufficient in order to get enough data to determine an accurate time threshold.

A generic time threshold can also be tuned to be more patient specific. In such a case, the IMD 100 is initially programmed to use a generic time threshold determined for a patient population. The time interval parameter is then determined for some detected arrhythmia events and information of these interval parameters are transmitted by the IMD 100 to the data processing unit. There the physician can investigate, based on other diagnostic data from the IMD 100 and/or from the patient, whether the default time threshold needs to be adjusted or tuned to be more accurate for the specific patient.

In a preferred embodiment, the R-wave detector 132 is configured to detect respective timings of R-waves during multiple cardiac cycles, preferably multiple consecutive cardiac cycles. The minimum detector 133 correspondingly detects the respective timings of cardiogenic impedance minima for these multiple cardiac cycles. The arrhythmia classifier 134 can then calculate multiple respective time intervals for these multiple cardiac cycles based on the respective timings of the R-waves and the associated cardiogenic impedance minima. The classification of an arrhythmia is then preferably performed based on these multiple time intervals.

The arrhythmia classifier 134 can then use a discrimination window that defines a number of consecutive cardiac cycles or a time length. In the former case, respective time intervals are determined for this number of cardiac cycles and in the latter case for the consecutive cardiac cycles that fall within the time length.

Each of the respective time intervals is preferably compared to the previously discussed time threshold and thereby generates an arrhythmia classification. The numbers of arrhythmia classifications according to the first type and the second type, respectively, are determined for the discrimination window. In a first embodiment, the arrhythmia type that was most common for the discrimination window is then selected by the arrhythmia classifier 134 as the conclusive arrhythmia class for that discrimination window. For instance, if 32 cardiac cycles are classified as SVT and 14 as VT from the onset of the arrhythmia until time out of the discrimination window, then the total episode could be classified as an SVT episode.

In an alternative approach, the number of cardiac cycles of the discrimination window that is classified according to one of the types or classes must reach a defined proportion of the total number of cardiac cycles for definitive classification. For instance, at least 60% of the cardiac cycles tested during the discrimination window needs to be classified by the arrhythmia classifier 134 to belong to the same arrhythmia class in order to classify the episode as being of that arrhythmia class.

The defined proportion can be fixed or be adaptive. An adaptive proportion is preferably a function of the heart rate of the heart. For instance, the number of cardiac cycles that should be classified as SVT could be increased with increasing cardiac rates.

If the number of cardiac cycles belonging to each class is identical according to the first embodiment above or whether the defined proportion of cardiac cycles is not exceeded for any of the arrhythmia classes according to the second embodiment various techniques can be taken by the IMD 100. In an embodiment, the arrhythmia classifier 134 automatically selects a defined default arrhythmia class, such as hemodynamically unstable arrhythmia or VT. The IMD 100 will then select an appropriate anti-arrhythmia scheme suitable for this default arrhythmia class, typically generation and application of a shock by the shock generator 144. In alternative embodiments, the discrimination window is either extended or restarted in order to try to classify the arrhythmia with sufficient certainty.

Animal studies have been conducted to verify that embodiments can be used to correctly classify arrhythmias induced in the test animals. The study was conducted on nine porcine. The animals were implanted with two pacemaker/ICD leads in the right atrium, two in the right ventricle and one in a left lateral coronary vein. An ICD can was also implanted in a pectoral position.

The first set of RA and RV leads was used to stimulate the heart very quickly in order to simulate a cardiac arrhythmia. Ventricular, supraventricular, hemodynamically stable and hemodynamically unstable arrhythmias were created.

Impedance data was measured from the second set of RA and RV leads and the LV lead in various configurations and the data was processed as disclosed herein in order to calculate the time interval from the timing of the R-wave to the timing of the cardiogenic impedance minimum.

In the experiments the impedance between two electrodes is measured by emitting small current pulses at a frequency of 128 Hz. The current pulses are preferably charge neutral and can, for instance, consist of a first negative pulse having a first duration, followed by a positive pulse having half the first duration and followed by a second negative pulse having the first duration. If the (positive) amplitude of the positive pulse is four times the (negative) amplitude of the two negative pulses charge neutrality is achieved. Examples of amplitudes that can be used include +250 µA and +750 µA for the positive pulse and −62.5 µA and −187.5 µA for the negative pulses. The pulse duration for the positive pulse can advantageously be in the interval of from 14 to 19 µs. The above presented example of current pulses should merely be seen as illustrative and non-limiting examples.

The resulting voltage is measured by a pair of electrodes. From the measured voltage signal and the emitted current pulses, the impedance between the voltage sensing electrodes is calculated by dividing the area of the measured voltage pulse by the area of the emitted current pulse.

For some impedance vectors mainly influenced by the atrial contraction, such as RA tip-RA ring bipolar and RA ring or tip-LV ring or tip bipolar, the systolic portion instead consists of a negative slope, i.e. as an inverted version of FIG. 4. For these impedance vectors, it is preferred if the impedance processor first inverts the signal before processing it further.

The impedance signal is then high pass filtered to remove the DC component that is present and to amplify the beat-to-beat variations in the signal. The filter used in the experiment had cutoff frequencies of 0.55 and 64 Hz. The resulting cardiogenic impedance signal is then processed as disclosed herein in order to derive the arrhythmia classification parameter, i.e. time interval.

Figure 5:
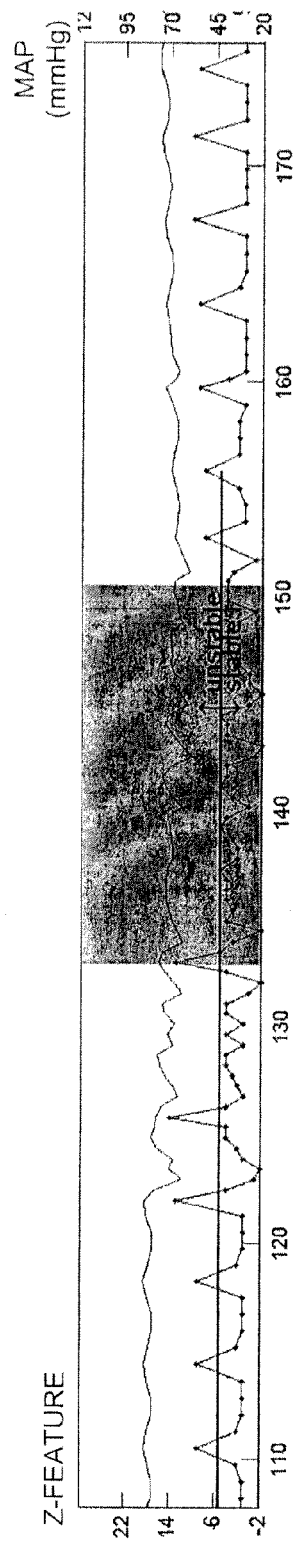
FIG. 5 schematically illustrates the Z feature and mean arterial pressure (MAP) over time for a subject suffering from a hemodynamically stable arrhythmia.
Figure 6:
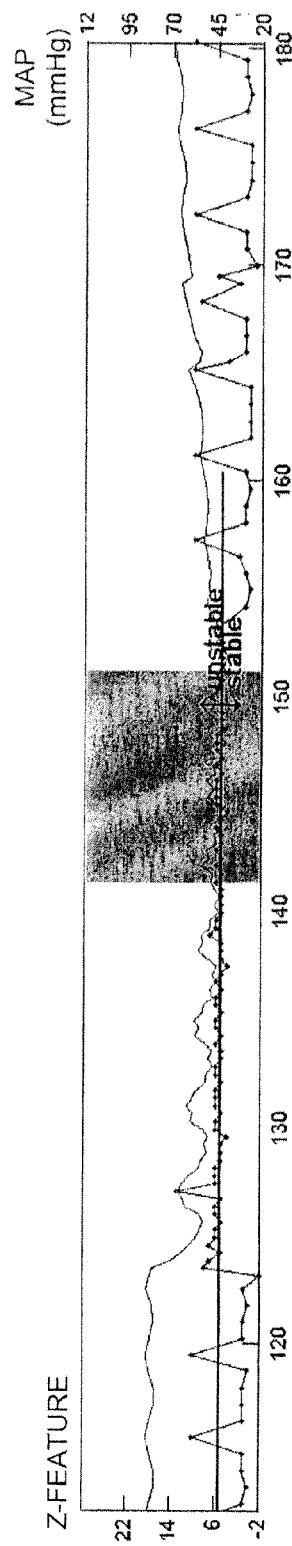
FIG. 6 schematically illustrates the Z-feature and mean arterial pressure (MAP) over time for a subject suffering from a hemodynamically unstable arrhythmia.

FIGS. 5 and 6 display the arrhythmia classification parameter, i.e. time interval, for a bipolar RA-LV impedance vector. The classification parameter is plotted together with the mean arterial pressure (MAP) over time. The length of a test episode is marked with gray. FIG. 5 illustrates a hemodynamically stable arrhythmia and as is seen in FIG. 5 the present invention correctly classifies the arrhythmia as being stable. In FIG. 6 the arrhythmia is instead hemodynamically unstable. The classification according to the invention is able to correctly identify the arrhythmia as unstable. The figures illustrate how the feature values below or above the threshold level (denoted by the black straight line in the figure) can be counted and how the classification can be made based on counting feature values above or below the threshold level.

Returning to FIG. 2, the controller 130 is further coupled to a memory 170 by a suitable data/address bus, wherein the programmable operating parameters used by the controller 130 are stored and modified, as required, in order to customize the operation of the IMD 100 to suit the needs of a particular patient. Such operating parameters define, for example, time threshold, pacing pulse amplitude, pulse duration, electrode polarity, rate, sensitivity, automatic features, and time interval between pacing pulse of an applied pacing pulse sequence.

The memory 170 may also advantageously store diagnostic data collected by the IMD 100. The diagnostic data include the IEGM signal from the data acquisition unit 160, the cardiogenic impedance signal from the impedance processor 131 and the classification data, including final classification and time interval parameter, from the arrhythmia classifier 134.

Advantageously, the operating parameters of the IMD 100 may be non-invasively programmed into the memory 170 through a transceiver 190 in communication via a communication link with the previously described communication unit of the programmer. The controller 130 activates the transceiver 190 with a control signal. The transceiver 190 can alternatively be implemented as a dedicated receiver and a dedicated transmitter connected to separate antennas or a common antenna, preferably a radio frequency (RF) antenna 195.

The IMD 100 additionally includes a battery 180 that provides operating power to all of the circuits shown in FIG. 2.

In the figure the impedance processor 131, the R-wave detector 132, the minimum detector 133, the arrhythmia classifier 134, the arrhythmia detector 135 and the maximum detector 136 has been exemplified as being run by the controller 130.

These units can then be implemented as a computer program product stored on the memory 170 and loaded and run on a general purpose or specially adapted computer, processor or microprocessor, represented by the controller 130 in the figure. The software includes computer program code elements or software code portions effectuating the operation of the impedance processor 131, the R-wave detector 132, the minimum detector 133, the arrhythmia classifier 134, the arrhythmia detector 135 and the maximum detector 136. The program may be stored in whole or part, on or in one or more suitable computer readable media or data storage means that can be provided in an IMD 100.

In an alternative embodiment, the impedance processor 131, the R-wave detector 132, the minimum detector 133, the arrhythmia classifier 134, the arrhythmia detector 135 and the maximum detector 136 are implemented as hardware units either forming part of the controller 130 or provided elsewhere in the IMD 100.

FIG. 7 is a flow diagram illustrating a method for classifying an arrhythmia of a heart of an animal subject, preferably a mammalian subject and more preferably a human subject. The method involves collecting a signal representative of electrical activity of at least a portion of the heart in step S1. The signal is preferably an IEGM signal collected by an IMD. An electric signal is applied in step S2 over a portion of the heart and the resulting electric signal is sensed in step S3 over a portion of the heart. Although the figure illustrates a serial implementation of steps S1-S3, the recording of the IEGM signal and the application of electric signal and measuring the resulting electric signal are preferably performed at least partly in parallel in order to record the IEGM signal during at least one cardiac cycle and perform steps S2 and S3 for the same at least one cardiac cycle.

A next step S4 determines a cardiogenic impedance signal based on information of the electric signal applied in step S2 and the resulting electric signal measured in step S3. The IEGM signal is processed in step S5 in order to detect the timing of an R-wave of at least one cardiac cycle in step S5. The next step S6 detects the timing of a cardiogenic impedance minimum in the cardiogenic impedance signal within the systolic time window. The two timings detected in steps S5 and S6 are utilized in step S7 to classify a detected arrhythmia as preferably either be of a type 1 or a type 2 arrhythmia.

The arrhythmia classification of step S7 is preferably performed based on the R-wave timings and the cardiogenic impedance minimum timings of multiple, preferably consecutive, cardiac cycles, which is schematically illustrated by the line L1.

FIG. 8 is a flow diagram illustrating an embodiment of the detecting step S6 in FIG. 7. The method continues from step S5 in FIG. 7. A next step S10 detects a local cardiogenic impedance minimum within a defined time window centered at the timing of the R-wave as detected in step S5. The next step S11 detects a cardiogenic impedance maximum in the search window having a start point defined based on the timing of the local cardiogenic impedance minimum detected in step S10 and an end point defined based on the timing of the R-wave of the next cardiac cycle. Finally, the cardiogenic impedance minimum is identified in step S12 in the systolic time window having a start point defined based on the timing of the local cardiogenic impedance minimum detected in step S10 and an end point coinciding with the timing of the cardiogenic impedance maximum detected in step S11. The method then continues to step S7 in FIG. 7.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

Although modifications and changes may be suggested by those skilled in the art, it is the intention of the inventor to embody within the patent warranted hereon all changes and modifications as reasonably and properly come within the scope of his contribution to the art.

We claim:

1. An implantable medical device for delivering cardiac therapy to a heart of a subject comprising:
    multiple electrodes;
    an electrode connector electrically connectable to said multiple electrodes of which at least one is arranged on a cardiac lead electrically connectable to said electrode connector;
    a data acquisition unit connected to said electrode connector and configured to collect a signal representative of electric activity of at least a portion of said heart;
    a signal generator connected to said electrode connector and configured to generate an electric signal applicable over two electrodes of said multiple electrodes;
    a signal sensing unit connected to the electrode connector and configured to sense a resulting electric signal over two electrodes of said multiple electrodes;
    an impedance processor configured to determine a cardiogenic impedance signal based on said electric signal generated by said signal generator and said resulting electric signal sensed by said signal sensing unit;
    an R-wave detector configured to detect a timing of an R-wave of said heart during a cardiac cycle based on said signal representative of said electric activity;
    a minimum detector configured to detect, based on said cardiogenic impedance signal, a timing of a cardiogenic impedance minimum within a systolic time window of a cardiac cycle; and
    an arrhythmia classifier configured to classify an arrhythmia of said heart based on said timing of said R-wave detected by said R-wave detector and said timing of said cardiogenic impedance minimum detected by said minimum detector.

2. The device according to claim 1, further comprising an arrhythmia detector configured to detect an arrhythmia of said heart based on a heart rate of said heart obtained from said signal representative of said electric activity.

3. The device according to claim 2, wherein said R-wave detector is responsive to said arrhythmia detector detecting said arrhythmia and is configured to detect said timing of said R-wave in response to said arrhythmia detector detecting said arrhythmia, and said minimum detector is responsive to said arrhythmia detector detecting said arrhythmia and is configured to detect said timing of said cardiogenic impedance minimum in response to said arrhythmia detector detecting said arrhythmia.

4. The device according to claim 1, wherein said arrhythmia classifier is configured to classify said arrhythmia based on a time interval from said timing of said R-wave detected by said R-wave detector to said timing of said cardiogenic impedance minimum detected by said minimum detector.

5. The device according to claim 4, wherein said arrhythmia classifier is configured to compare said time interval to a time threshold and classify said arrhythmia based on said comparison.

6. The device according to claim 1, wherein said minimum detector is configured to detect a local cardiogenic impedance minimum within a defined time window centered at said timing of said R-wave detected by said R-wave detector,
    said implantable medical device further comprising a maximum detector configured to detect, based on said cardiogenic impedance signal, a cardiogenic impedance maximum in a search window having a start point defined based on said local cardiogenic impedance minimum detected by said minimum detector and an end point defined based on a timing of said R-wave detected by said R-wave detector for a following cardiac cycle,
    said minimum detector is configured to detect said timing of said cardiogenic impedance minimum within said systolic time window having a start point defined based on said local cardiogenic impedance minimum detected by said minimum detector and an end point defined based on said cardiogenic impedance maximum detected by said maximum detector.

7. The device according to claim 6, wherein said maximum detector is configured to detect, based on said cardiogenic impedance signal, a cardiogenic impedance maximum in a search window extending from a fixed time interval following said local cardiogenic impedance minimum detected by said minimum detector and to said timing of said R-wave detected by said R-wave detector for said following cardiac cycle plus a delta equal to said timing of said R-wave detected by said R-wave detector for said cardiac cycle subtracted by a timing of said local cardiogenic impedance minimum detected by said minimum detector,
    said minimum detector is configured to detect said timing of said cardiogenic impedance minimum within said systolic time window extending from said fixed time interval following said local cardiogenic impedance minimum detected by said minimum detector and up to said cardiogenic impedance maximum detected by said maximum detector.

8. The device according to claim 6, wherein said minimum detector is configured to detect, based on said cardiogenic impedance signal, said local cardiogenic impedance minimum within a defined time window of .+−.50 ms relative said timing of said R-wave detected by said R-wave detector.

9. The device according to claim 1, further comprising: a maximum detector configured to detect, based on said cardiogenic impedance signal, a cardiogenic impedance maximum in a search window having a start point at a fixed time interval before said timing of said R-wave detected by said R-wave detector and an end point defined based on a timing of said R-wave detected by said R-wave detector for a following cardiac cycle; and said minimum detector is configured to detect said timing of said cardiogenic impedance minimum within said systolic time window having a start point at said fixed time interval before said timing of said R-wave detected by said R-wave detector and an end point defined based on said cardiogenic impedance maximum detected by said maximum detector.

10. The device according to claim 1, wherein said arrhythmia classifier is configured to classify said arrhythmia as being a hemodynamically stable arrhythmia or a hemodynamically unstable arrhythmia based on said timing of said R-wave detected by said R-wave detector and said timing of said cardiogenic impedance minimum detected by said minimum detector.

11. The device according to claim 10, further comprising:
a shock generator connected to said electrode connector and configured to generate a defibrillation shock applicable to at least a portion of said heart; and
a controller connected to said shock generator and configured to activate said shock generator if said arrhythmia classifier classifies said arrhythmia as a hemodynamically unstable arrhythmia and prevent said shock generator from generating said defibrillation shock if said arrhythmia classifier classifies said arrhythmia as a hemodynamcially stable arrhythmia.

12. The device according to claim 1, wherein said arrhythmia classifier is configured to classify said arrhythmia as being a supraventricular tachycardia or ventricular tachycardia based on said timing of said R-wave detected by said R-wave detector and said timing of said cardiogenic impedance minimum detected by said minimum detector.

13. The device according to claim 12, further comprising:
a shock generator connected to said electrode connector and configured to generate a defibrillation shock applicable to at least a portion of said heart; and
a controller connected to said shock generator and configured to activate said shock generator if said arrhythmia classifier classifies said arrhythmia as a ventricular tachycardia and prevent said shock generator from generating said defibrillation shock if said arrhythmia classifier classifies said arrhythmia as a supraventricular tachycardia.

14. The device according to claim 1, wherein said R-wave detector is configured to detect respective timings of R-waves during multiple cardiac cycles based on said signal representative of said electric activity;
said minimum detector is configured to detect, based on said cardiogenic impedance signal, respective timings of cardiogenic impedance minima within systolic time windows of said multiple cardiac cycles; and
said arrhythmia classifier is configured to calculate a respective time interval from respective timing of said R-wave to respective timing of said cardiogenic impedance minimum for each of said multiple cardiac cycles and classify said arrhythmia based on said respective time intervals.

15. The device according to claim 14, wherein said arrhythmia classifier is configured to compare said respective time intervals to a time threshold and classify said arrhythmia as being of a first arrhythmia type if a pre-defined number of said respective time intervals exceed said time threshold and classify said arrhythmia as being of a second arrhythmia type if a pre-defined number of said respective time intervals is below said time threshold.

* * * * *